(12) United States Patent
Shinoda et al.

(10) Patent No.: US 9,861,984 B2
(45) Date of Patent: Jan. 9, 2018

(54) MICROCHIP AND CHANNEL STRUCTURE FOR THE SAME

(71) Applicant: Sony Corporation, Tokyo (JP)

(72) Inventors: Masataka Shinoda, Tokyo (JP); Toru Takashimizu, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/221,261

(22) Filed: Jul. 27, 2016

(65) Prior Publication Data

US 2016/0332162 A1 Nov. 17, 2016

Related U.S. Application Data

(63) Continuation of application No. 14/250,003, filed on Apr. 10, 2014, now Pat. No. 9,409,172, which is a
(Continued)

(30) Foreign Application Priority Data

| May 13, 2008 | (JP) | 2008-125946 |
| Aug. 1, 2008 | (JP) | 2008-199585 |
| Nov. 11, 2008 | (JP) | 2008-288896 |

(51) Int. Cl.
*B01L 3/00* (2006.01)
*G05D 7/06* (2006.01)
(Continued)

(52) U.S. Cl.
CPC ..... *B01L 3/502776* (2013.01); *B01J 19/0093* (2013.01); *B01L 3/502761* (2013.01);
(Continued)

(58) Field of Classification Search
CPC ............ B01J 19/0093; B01J 2219/0853; B01J 2219/00889; B01J 2219/00891;
(Continued)

(56) References Cited

U.S. PATENT DOCUMENTS

| 3,649,829 A | 3/1972 | Randolf |
| 4,756,427 A | 7/1988 | Gohde et al. |

(Continued)

FOREIGN PATENT DOCUMENTS

| DE | 102 060 083 | 8/2003 |
| EP | 1 481 723 | 12/2004 |

(Continued)

OTHER PUBLICATIONS

European Search Report dated Nov. 27, 2015 in corresponding European Application No. 15001193.0.
(Continued)

*Primary Examiner* — Jennifer Wecker
(74) *Attorney, Agent, or Firm* — K&L Gates LLP

(57) ABSTRACT

A microchip includes a channel permitting a sheath liquid to flow therethrough; and a microtube for introducing a sample liquid into a laminar flow of the sheath liquid flowing through the channel; wherein liquid feeding is performed in the condition where a laminar flow of the sample liquid introduced through the microtube is surrounded by the laminar flow of the sheath liquid.

16 Claims, 10 Drawing Sheets

Related U.S. Application Data continuation of application No. 12/435,160, filed on May 4, 2009, now abandoned.

(51) Int. Cl.
  *F15C 1/04* (2006.01)
  *B07C 3/02* (2006.01)
  *G01N 15/14* (2006.01)
  *B01J 19/00* (2006.01)
  G01N 15/10 (2006.01)
  G01N 35/10 (2006.01)

(52) U.S. Cl.
  CPC .... *B01L 3/502784* (2013.01); *G01N 15/1404* (2013.01); *B01J 2219/00853* (2013.01); *B01J 2219/00889* (2013.01); *B01J 2219/00891* (2013.01); *B01L 2200/0647* (2013.01); *B01L 2200/0652* (2013.01); *B01L 2200/0673* (2013.01); *B01L 2300/0645* (2013.01); *B01L 2300/0861* (2013.01); *B01L 2400/02* (2013.01); *G01N 35/10* (2013.01); *G01N 2015/1037* (2013.01); *G01N 2015/1406* (2013.01); *G01N 2015/149* (2013.01); *Y10T 137/0324* (2015.04); *Y10T 137/2191* (2015.04)

(58) Field of Classification Search
  CPC ..... B01L 2300/0861; B01L 2200/0652; B01L 2400/02; B01L 3/502761; B01L 3/502776; B01L 3/502784; G01N 15/1404; G01N 2015/1037; G01N 2015/1406; G01N 2015/149; G01N 35/10; Y10T 137/0324; Y10T 137/2191
  See application file for complete search history.

(56) References Cited

U.S. PATENT DOCUMENTS

| | | | |
|---|---|---|---|
| 4,936,465 A * | 6/1990 | Zold | B07C 3/02 209/3.1 |
| 4,954,715 A | 9/1990 | Zold | |
| 5,007,732 A | 4/1991 | Ohki et al. | |
| 5,194,909 A | 3/1993 | Tycko | |
| 5,439,578 A | 8/1995 | Dovichi et al. | |
| 5,741,412 A | 4/1998 | Dovichi et al. | |
| 6,263,745 B1 | 7/2001 | Buchanan et al. | |
| 6,365,106 B1 | 4/2002 | Nagai | |
| 6,473,171 B1 | 10/2002 | Buttry et al. | |
| 6,809,804 B1 | 10/2004 | Yount et al. | |
| 7,245,379 B2 | 6/2007 | Schwabe | |
| 2003/0044832 A1 | 3/2003 | Blankenstein | |
| 2003/0175980 A1 | 9/2003 | Hayenga et al. | |
| 2003/0209059 A1 | 11/2003 | Kawano et al. | |
| 2004/0069632 A1 | 4/2004 | Ripoll et al. | |
| 2005/0105079 A1 | 5/2005 | Pletcher et al. | |
| 2005/0123450 A1 | 6/2005 | Gilbert et al. | |
| 2005/0153458 A1 | 7/2005 | Van den Engh | |
| 2006/0078888 A1 | 4/2006 | Griffiths et al. | |
| 2006/0163385 A1 | 7/2006 | Link et al. | |
| 2006/0166375 A1 | 7/2006 | Hawkins et al. | |
| 2007/0184489 A1 | 8/2007 | Griffiths et al. | |
| 2007/0215528 A1 | 9/2007 | Hayenga et al. | |

FOREIGN PATENT DOCUMENTS

| | | |
|---|---|---|
| EP | 1481723 | 12/2004 |
| JP | 2003-107099 | 4/2003 |
| JP | 2004-531365 | 10/2004 |
| JP | 2005-513476 | 5/2005 |
| JP | 2006-017562 | 1/2006 |
| JP | 2006-071388 | 3/2006 |
| JP | 2006-523142 | 10/2006 |
| KR | 1020050047540 | 5/2005 |
| WO | 2007/072002 | 11/2009 |

OTHER PUBLICATIONS

Partial European Search Report dated Aug. 10, 2015 in corresponding European Application No. 15001193.0.
Korean Office Action dated Apr. 14, 2015 in corresponding Korean Application No. 10-2009-0032376.
Summons to attend oral proceedings pursuant to Rule 115(1) EPC issued Oct. 14, 2014 in corresponding European Application No. 09005640.9.
Japanese Office Action issued Jun. 29, 2010 for corresponding Japanese Patent Application No. 2008-288896.
International Search Report dated Jul. 23, 2009, for corresponding Patent Application EP 09005640.9.
Study on Micro Total Analysis System, Hiroyuki Yamada, et al., Yamanashi Industrial Technology Center, Faculty of Engineering, Toyo University.

* cited by examiner

MICROCHIP AND CHANNEL STRUCTURE FOR THE SAME

CROSS REFERENCES TO RELATED APPLICATIONS

The present application is a continuation application of U.S. patent application Ser. No. 14/250,003, filed Apr. 10, 2014, which application is a continuation application of U.S. patent application Ser. No. 12/435,160, filed May 4, 2009, which application claims priority to that disclosed in Japanese priority Patent Application JP 2008-125946, JP 2008-199585, and JP 2008-288896 filed in the Japan Patent Office on May 13, 2008, on Aug. 1, 2008, and on Nov. 11, 2008 the entire contents of which are hereby incorporated by reference.

BACKGROUND

The present application relates to a microchip and a channel structure for the same. More particularly, the invention relates, for example, to a microchip which is provided with a channel or channels for performing chemical and biological analyses and in which liquid feeding is conducted in the condition where a laminar flow of a sample liquid is surrounded by a laminar flow of a sheath liquid in the channels.

In recent years, microchips have been developed in which an area and/or a channel or channels for performing chemical and biological analyses are provided by application of micro-machining techniques used in the semiconductor industry. These microchips have begun to be utilized for electrochemical detectors in liquid chromatography, small electrochemical sensors in medical service sites, and the like.

Analytical systems using such microchips are called μ-TAS (micro-Total-Analysis System), lab-on-a-chip, bio chip or the like, and is paid attention to as a technology by which chemical and biological analyses can be enhanced in speed, efficiency and level of integration or by which analyzing apparatuses can be reduced in size.

The μ-TAS, which enables analysis with a small amount of sample and enables disposable use of microchips, is expected to be applied particularly to biological analyses where precious trace amounts of samples or a multiplicity of specimens are treated.

An application example of the μ-TAS is a particulate analyzing technology in which characteristics of particulates such as cells and microbeads are analyzed optically, electrically or magnetically in channels arranged on microchips. In the particulate analyzing technology, fractional collection of a population satisfying a predetermined condition or conditions from among particulates on the basis of analytical results of the particulates is also conducted.

For example, Japanese Patent Laid-open No. 2003-107099 (hereinafter referred to as Patent Document 1) discloses "a particulate fractionation microchip having a channel for introducing particulate-containing solution, and a sheath flow forming channel arranged on at least one lateral side of the introducing channel." The particulate fractionation microchip further has "a particulate measuring section for measuring the particulates introduced, at least two particulate fractionating channels disposed on the downstream side of the particulate measuring section so as to perform fractional collection of the particulates, and at least two electrodes disposed in the vicinity of channel ports opening from the particulate measuring section into the particulate fractionating channels so as to control the moving direction of the particulates."

The particulate fractionation microchip disclosed in Patent Document 1, typically, is so designed that fluid laminar flows are formed by a "trifurcated channel" having a channel for introducing a particulate-containing solution and two sheath flow forming channels (see "FIG. 1" of the document).

FIGS. 13A and 13B show an ordinary trifurcated channel structure (FIG. 13A), and sample liquid and sheath laminar flows (FIG. 13B) formed by the channel structure. In the trifurcated channel, a sample liquid laminar flow passing through a channel 101 in the direction of solid-line arrow in FIG. 13A can be sandwiched, from the left and right sides, by sheath liquid laminar flows introduced through channels 102, 102 in the directions of dotted-line arrows in the figure. By this, as shown in FIG. 13B, the sample liquid laminar flow can be fed through the center of the channel. Incidentally, in FIG. 13B, the sample liquid laminar flow is depicted in solid lines, and the channel structure in dotted lines.

In the particulate fractionation microchip disclosed in Patent Document 1, the trifurcated channel ensures that the particulate-containing solution is sandwiched by the flows of the sheath liquid from the left and right sides, and the particulates are made to flow through the center of the channel in the particulate measuring section. As a result, in the case of measuring the particulates optically, for example, each of the particulates can be accurately irradiated with measuring light.

SUMMARY

According to the trifurcated channel shown in FIGS. 13A and 13B, the sample liquid laminar flow is sandwiched by the sheath liquid laminar flows from the left and right sides, whereby with respect to the sandwiching direction (the Y-axis positive-negative direction in FIGS. 13A and 13B), the sample liquid laminar flow can be fed in the state of being deflected to an arbitrary position in the channel. With respect to other directions, for example, the vertical direction (the Z-axis positive-negative direction in FIGS. 13A and 13B) of the channel, however, it has been very difficult to control the sample liquid feeding position. In other words, in the trifurcated channel shown in FIGS. 13A and 13B, it has only been possible to form the sample laminar flow that is oblong (in section) in the Z-axis direction.

Therefore, the microchip having a trifurcated channel according to the related art has the problem that in the case where, for example, a particulate-containing solution as a sample liquid is made to flow through a channel and subjected to optical analysis, there would be a dispersion of the feeding position of the particulates in the vertical direction (depth direction) of the channel. Consequently, it has been very difficult to accurately irradiate each of the particulates with measuring light.

Particularly, in the case of analysis of cells such as blood corpuscle cells, the cells are fed in the manner of rolling on the bottom surface of a channel, and there would be a large discrepancy between the cell feeding position and the focal position of the measuring light in the vertical direction (depth direction) of the channel, causing a lowering in accuracy of analysis.

Thus, there is a need for a microchip in which sandwiching (surrounding) of a sample liquid laminar flow by sheath liquid laminar flow(s) can be achieved also in the vertical direction (depth direction) of a channel and by which a high accuracy of analysis can be obtained.

According to an embodiment, there is provided a microchip including a channel permitting a sheath liquid to flow therethrough, and a microtube for introducing a sample liquid into a laminar flow of the sheath liquid flowing through the channel. In the microchip, the sample liquid is introduced into a laminar flow of the sheath liquid by a microtube, whereby liquid feeding can be performed in the condition where a laminar flow of the sample liquid is surrounded by the laminar flow of the sheath liquid. As the microtube, a plurality of microtubes may be arranged in a bundled state, and the sample liquid may be introduced via at least one of the plurality of the microtubes.

In the microchip, the channel may have a narrow-down section in which its area in a section orthogonal to the liquid feed direction decreases gradually or stepwise along the liquid feed direction. With the narrow-down section, the sheath liquid laminar flow and the sample liquid laminar flow are made to pass while the laminar flow widths of the laminar flows are narrowed down.

The narrow-down section, preferably, is so formed that its area in the section orthogonal to the liquid feed direction decreases gradually. Particularly desirably, one of a channel bottom surface and a channel upper surface of the narrow-down section is formed as an inclined surface. With one of the channel bottom surface and the channel upper surface of the narrow-down section formed as an inclined surface, the sheath liquid laminar flow and the sample liquid laminar flow can be made to pass while being deflected toward the upper side or the lower side of the microchip and being narrowed down.

In addition, of the narrow-down section, both the channel bottom surface and the channel upper surface may be formed as inclined surfaces. Besides, at least one of the channel bottom surface and the channel upper surface may be formed in a stairway-like shape so that the area in the section orthogonal to the liquid feed direction decreases stepwise. Further, a channel side wall may be formed in the manner of gradual or stepwise constriction along the liquid feed direction.

In the microchip, the microtube may be formed from a metal permitting a voltage to be impressed thereon. With the microtube formed from a metal permitting a voltage to be impressed thereon, an electric charge can be imparted to the sample liquid flowing inside the microtube.

In this case, the channel may be provided with branch channels branching from the channel on the downstream side of the narrow-down section of the channel, whereby the flow direction, at the branching section of the branch channels, of the sample liquid given the electric charge can be controlled by electrodes disposed at the branching section.

Furthermore, the channel may be provided with a fluid introduction section which joins the channel on the upstream side of the branching section from at least one lateral side and through which either fluid of a gas and an insulating liquid is introduced into the channel, whereby the sheath liquid laminar flow and the sample liquid laminar flow passing through the channel can be made to pass while being split into droplets by the fluid introduced via the fluid introduction section. Or, alternatively, a piezoelectric element capable of giving a pressure difference to the sample liquid flowing through the microtube may be provided, whereby the sample liquid can be introduced in a dropletized state (in the state of having been split into droplets) into the sheath liquid laminar flow passing through the channel. With such an arrangement, the sample liquid containing particulates can be dropletized and, simultaneously, given an electric charge, which makes it possible to control the liquid feed direction at the branching section.

According to an embodiment, there are provided a fluid analyzing apparatus and a particulate fractionating apparatus on each of which the above-mentioned microchip can be mounted.

In addition, according to another embodiment, there is provided a channel structure including a channel permitting a fluid to flow therethrough, and a microtube for introducing another fluid into a laminar flow of the fluid flowing through the channel. With this channel structure, fluid feeding can be performed in the condition where a laminar flow of the another fluid introduced through the microtube is surrounded by the laminar flow of the fluid flowing through the channel.

Further, according to a further embodiment, there is provided a liquid feeding method for a microchip channel, wherein a sample liquid is introduced by a microtube into a laminar flow of a sheath liquid flowing through a channel, and liquid feeding is performed in the condition where a laminar flow of the sample liquid is surrounded by the laminar flow of the sheath liquid.

In the liquid feeding method, the sample liquid, with an electric charge given thereto by a metallic microtube permitting a voltage to be impressed thereon, may be introduced into the laminar flow of the sheath liquid flowing through the channel having a branching section, whereby the flow direction, at the branching section of the channel, of the sample liquid can be controlled by electrodes disposed at the branching section.

In this case, either fluid of a gas and an insulating liquid may be introduced into the channel through which the sheath liquid laminar flow and the sample liquid laminar flow pass, whereby the sheath liquid laminar flow and the sample liquid laminar flow which are flowing can be split into droplets and, simultaneously, an electric charge can be given to the sample liquid by the metallic microtube. Or, alternatively, a pressure difference may be applied by a piezoelectric element to the sample liquid flowing through the microtube, whereby the sample liquid can be introduced in a dropletized state into the laminar flow of the sheath liquid flowing through the channel and, simultaneously, an electric charge can be given to the sample liquid by the metallic microtube. With such a configuration, it is possible to dropletize the sample liquid containing particulates and, simultaneously, to give an electric charge to the sample liquid, so as thereby to control the liquid feed direction at the branching section.

Thus, according to an embodiment, there is provided a microchip in which sandwiching (surrounding) of a sample liquid laminar flow by sheath liquid laminar flow(s) can be achieved also in the vertical direction (depth direction) of a channel and by which a high accuracy of analysis can be obtained.

Additional features and advantages of the present application are described in, and will be apparent from, the following Detailed Description of the Invention and the figures.

BRIEF DESCRIPTION OF THE FIGURES

FIGS. 2A and 2B are sectional schematic views showing a sheath liquid laminar flow and a sample liquid laminar flow which are formed inside a channel in the microchip 1, in which FIG. 2A shows section P-P, and FIG. 2B shows section Q-Q, of the magnified view in FIG. 1;

FIGS. 4A and 4B are sectional schematic views showing the sheath liquid laminar flow and the sample liquid laminar flow on the upstream side (FIG. 4A) and the downstream side (FIG. 4B) of a narrow-down section in the microchip 1, wherein FIG. 4A shows section $R_1$-$R_1$ of FIG. 2, and FIG. 4B shows section $R_2$-$R_2$ of FIG. 2;

FIGS. 11A and 11B are schematic views showing a joining section of the microchip 3 in an enlarged form, in which FIG. 11A is a top plan view, and FIG. 11B is a sectional view taken along ZX plane containing a microtube;

DETAILED DESCRIPTION

Figure 1:
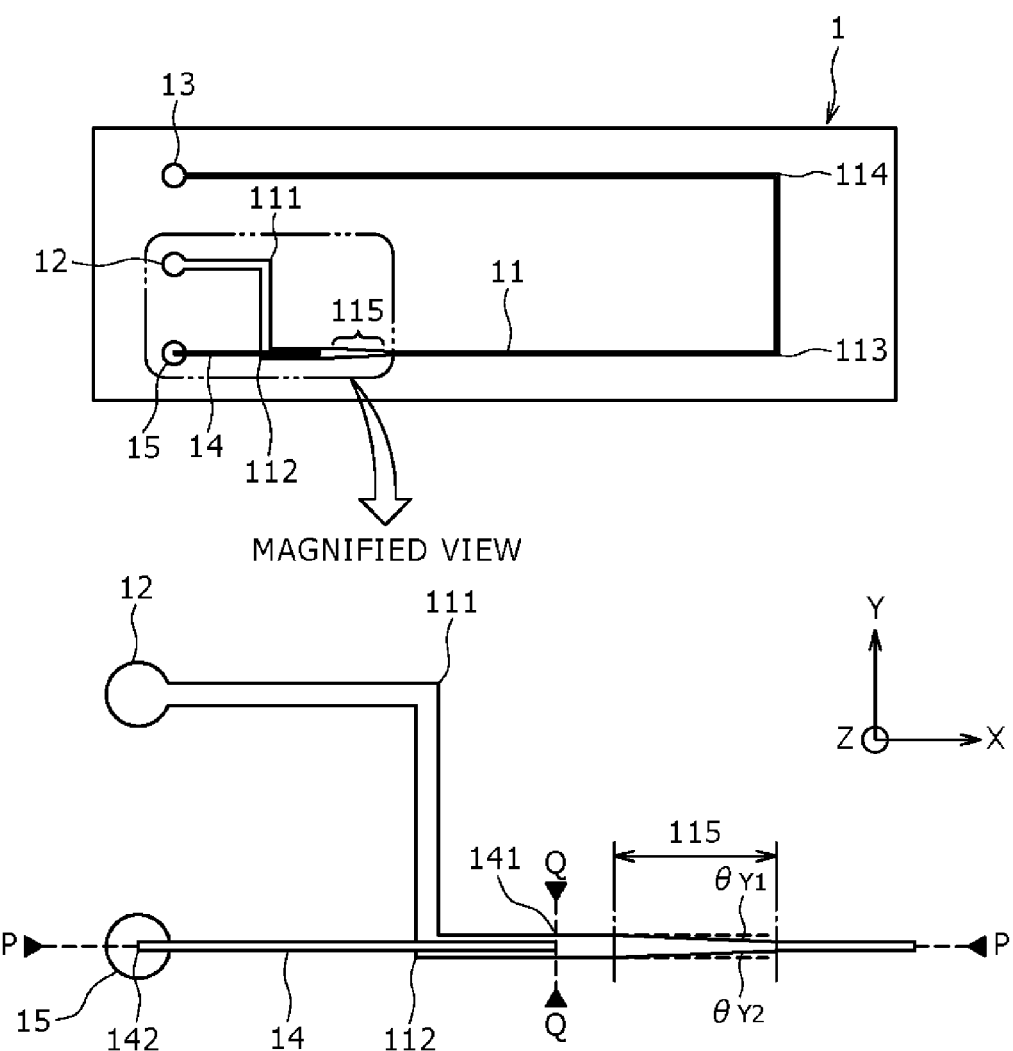
FIG. 1 is a simplified top plan view showing the configuration of a microchip 1 according to an embodiment.

The present application will be described below referring to the drawings according to an embodiment.

1. Microchip

FIG. 1 is a simplified top plan view showing the configuration of a microchip according to an embodiment.

A microchip denoted by symbol 1 in FIG. 1 is provided therein with a channel 11 including bent sections 111, 112, 113, 114 where the channel 11 is bent at about 90 degrees. In FIG. 1, symbol 12 denotes a sheath liquid inlet for introducing a sheath liquid into the channel 11, and symbol 13 denotes an outlet for discharging the sheath liquid and the like to the exterior of the channel 11. The sheath liquid introduced through the sheath liquid inlet 12 into the channel 11 is fed while being deflected by about 90 degrees at the bent sections 111, 112, 113, 114, and is discharged via the outlet 13.

(1-1) Microtube

At the bent section 112 of the channel 11, a microtube 14 is arranged for introducing a sample liquid into the laminar flow of the sheath liquid flowing through the channel 11. In FIG. 1, symbol 15 denotes a sample liquid inlet for introducing the sample liquid into the microtube 14, symbol 141 denotes an opening of the microtube 14 at an end on the side of the channel 11, and symbol 142 denotes an opening of the microtube 14 at an end on the side of the sample liquid inlet 15. The sample liquid supplied from the sample liquid inlet 15 into the opening 142 flows through the microtube 14, to be introduced via the opening 141 into the laminar flow of the sheath liquid flowing through the channel 11.

In the microchip 1, the sample liquid is thus introduced through the microtube 14 into the sheath liquid laminar flow passing through the channel 11, whereby liquid feeding can be performed in the condition where the sample liquid laminar flow is surrounded by the sheath liquid laminar flow.

(1-2) Narrow-Down Section

In FIG. 1, symbol 115 denotes a narrow-down section provided in the channel 11. The narrow-down section 115 is so formed that its area in section orthogonal to the liquid feed direction decreases gradually along the direction from the upstream side toward the downstream side of the channel 11. Specifically, channel side walls of the narrow-down section 115 are so formed that the channel size is gradually constricted in the Y-axis direction in the figure along the liquid feed direction. Thus, the shape of the narrow-down section 115 can be deemed as a spindle-like shape gradually decreased in width in top plan view. With this shape, the narrow-down section 115 ensures that the sheath liquid laminar flow and the sample liquid laminar flow can be made to pass while the laminar flow widths are narrowed down in the Y-axis direction in the figure. Furthermore, the narrow-down section 115 is so formed that the channel bottom surface is an inclined surface which becomes higher in the depth direction (Z-axis direction in the figure) along the downstream direction. This ensures that the laminar widths can be narrowed down also in the depth direction (this will be described in detail below).

2. Formation of Laminar Flow by Microtube

Figure 2A:
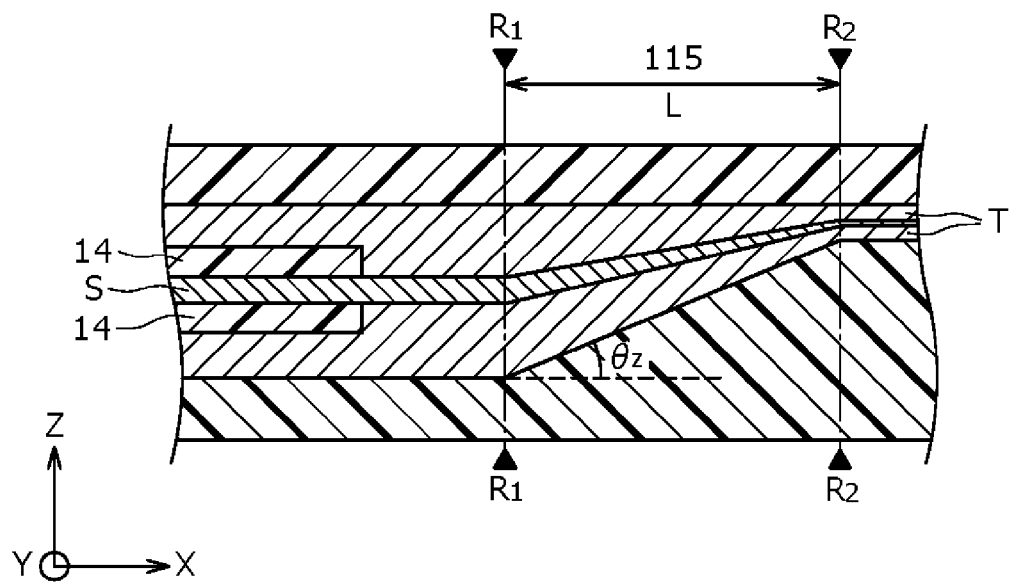
Figure 2B:
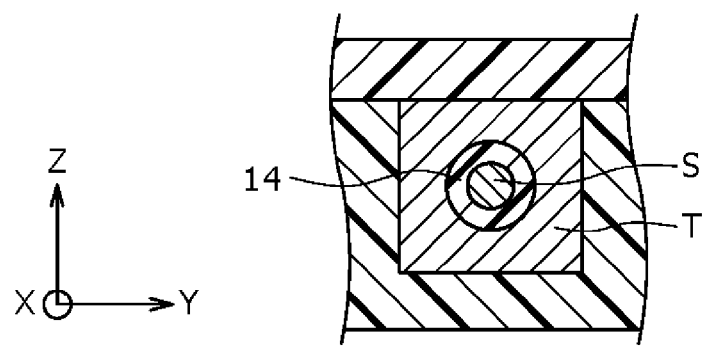

FIGS. 2A and 2B are schematic views showing the sheath liquid laminar flow and the sample liquid laminar flow which are formed inside the channel 11. FIG. 2A is a sectional schematic view corresponding to section P-P of the magnified view in FIG. 1, and shows the opening 141 of the microtube 14 and the narrow-down section 115 of the channel 11 in a magnified form. FIG. 2B is a sectional schematic view corresponding to section Q-Q of the magnified view in FIG. 1, and shows in a magnified form the opening 141 as frontly viewed from the downstream side of the channel.

The sample liquid is introduced by the microtube 14 into the sheath liquid laminar flow (see symbol T in the figures) passing through the channel 11, whereby liquid feeding can be performed in the condition where the sample liquid laminar flow (see symbol S in the figures) is surrounded by the sheath liquid laminar flow T, as shown in FIG. 2A.

FIGS. 2A and 2B shows the case where the microtube 14 is so disposed that its center is located coaxially with the center of the channel 11. In this case, the sample liquid laminar flow S is introduced into the center of the sheath liquid laminar flow T passing through the channel 11. The formation position of the sample liquid laminar flow S in the sheath liquid laminar flow T can be set arbitrarily, by regulating the layout position of the microtube 14 in the channel 11.

Figure 3:
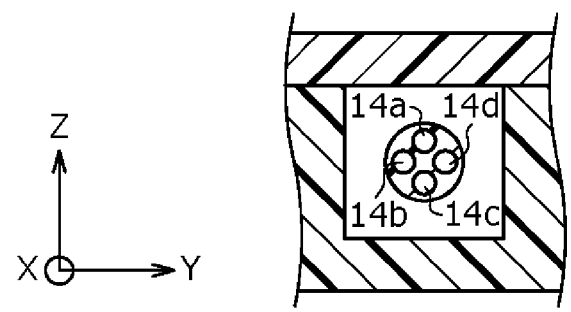
FIG. 3 is a sectional schematic view of each of a plurality of microtubes arranged in a bundled state, the figure corresponding to section Q-Q of the magnified view in FIG. 1.

In addition, FIGS. 2A and 2B shows the case where the microtube 14 is arranged as a single tube. The microtube 14 is not limited to this arrangement. For example, as shown in FIG. 3, the microtube 14 may be a bundle of a plurality of tubes (in the figure, four tubes). Where a bundle of tubes are used as the microtube, the sample liquid can be introduced through any one of, for example, microtubes 14a, 14b, 14c, 14d, and other solvent(s) than the sample liquid and the sheath liquid can be introduced through other one(s) of the microtubes 14a, 14b, 14c, 14d. Incidentally, FIG. 3 shows the case where the bundling is achieved by integrally forming the four microtubes 14a, 14b, 14c, 14d.

More specifically, a mode can be considered in which, for example, a sample liquid containing particulates is introduced through the microtube 14a, and a solution(s) containing a substance(s) capable of reaction with the particulates is introduced through the microtubes 14b, 14c, 14d so that the particulates react with the substance(s) in the laminar flow formed inside the channel 11. Examples of the substance(s) capable of reaction with the particulates include an antibody to be bonded to the surfaces of the particulates, and a compound capable of chemical reaction with the particulates.

As will be described later, in the case where a particulate-containing solution is made to flow through the channel as a sample liquid and the particulates are subjected to optical analysis and/or sampling, an antibody to be bonded to the surfaces of the particulates may be introduced at the time of forming the sample liquid laminar flow, whereby analysis and/or sampling of the particulates can be performed based on a fluorescent label possessed by the antibody bonded to the particulates. Besides, where a compound capable of chemical reaction with the particulates is introduced, it is possible to detect the reaction between the particulates and the compound inside the channel 11 and, based on the presence or absence of the reaction, to perform analysis and/or sampling of the particulates.

The number of the microtubes bundled together can be two or more, and the number may be arbitrarily set according to the numbers of the sample liquid(s) and solvent(s) to be introduced. In addition, at the opening of each microtube at the opposite side of an end on the side of the channel 11, a configuration for supplying the respective sample liquid or solvent, like the sample liquid inlet 15, is provided.

3. Narrowing-Down of Laminar Flow Width by Narrow-Down Section

The narrow-down section 115 is so formed that its area in section orthogonal to the liquid feed direction decreases gradually along the downstream direction of the channel. Specifically, as shown in FIG. 2A, the narrow-down section 115 is so formed that its channel bottom surface is an inclined surface which becomes higher, in the Z-axis direction in the figure, along the downstream direction. This shape ensures that the sheath liquid laminar flow and the sample liquid laminar flow fed into the narrow-down section 115 pass while being deflected toward the side of the upper surface of the microchip 1 and being narrowed down in laminar flow width in the Z-axis direction in the figure.

Figure 4A:
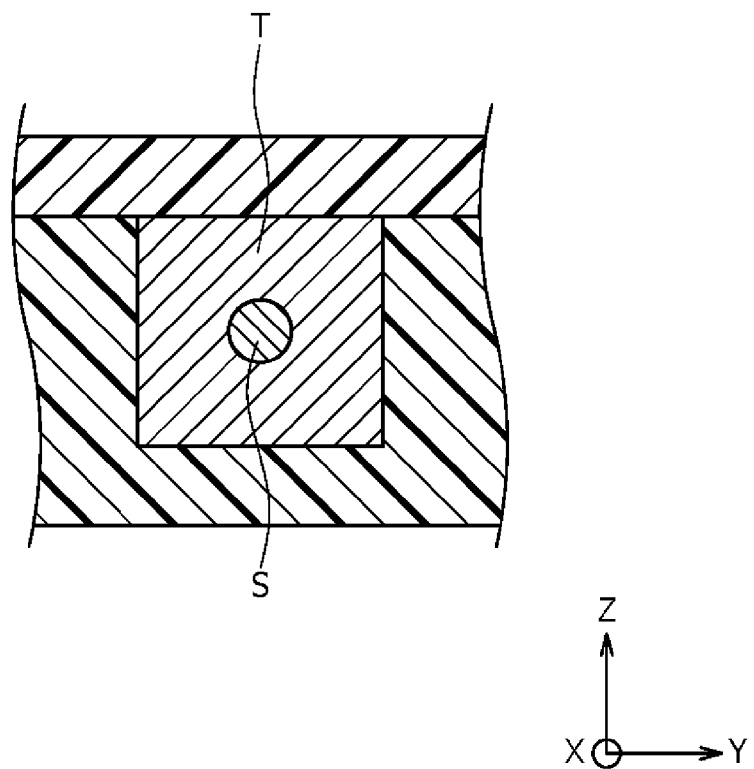
Figure 4B:
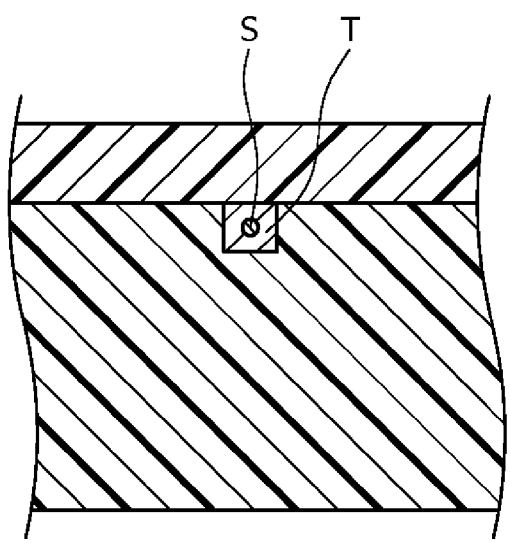

FIGS. 4A and 4B are schematic views showing the sheath liquid laminar flow and the sample liquid laminar flow on the upstream side (FIG. 4A) and the downstream side (FIG. 4B) of the narrow-down section 11. FIG. 4A is a sectional schematic view corresponding to section R1-R1 in FIG. 2A, and FIG. 4B is a sectional schematic view corresponding to section R2-R2 in FIG. 2A.

As has been described above referring to FIG. 1, the narrow-down section 115 is formed in a spindle-like shape gradually decreased in size in the Y-axis direction along the downstream direction. In addition, as has been described above referring to FIGS. 2A and 2B, the channel bottom surface of the narrow-down section 115 is formed as an inclined surface which becomes higher in the Z-axis direction along the downstream direction. Thus, the narrow-down section 115 is so formed that its area in section orthogonal to the liquid feed direction decreases along the downstream direction of the channel, whereby the sheath liquid laminar flow T and the sample liquid laminar flow S can be made to pass while being narrowed down in laminar flow width in the Y-axis and Z-axis directions and while being deflected toward the upper side of the microchip 1 (in the Z-axis positive direction in FIGS. 4A and 4B). Specifically, the sheath liquid laminar flow T and the sample liquid laminar flow S shown in FIG. 4A are made to pass while their laminar flow widths are narrowed down in the narrow-down section 115, as shown in FIG. 4B.

Thus, liquid feeding is performed while the laminar flow widths of the sheath liquid laminar flow and the sample liquid laminar flow are narrowed down. This ensures that in the case where, for example, a solution containing particulates is made to flow through the channel as a sample liquid and optical analysis of the particulates is conducted, the particulates in the sample liquid laminar flow thus narrowed down can be accurately irradiated with measuring light. Particularly, according to the narrow-down section 115, the laminar flow width of the sample liquid laminar flow can be narrowed down not only in the horizontal direction (Y-axis direction in FIG. 1) of the microchip 1 but also in the vertical direction (Z-axis direction in FIGS. 2A and 2B). Therefore, the focal position of the measuring light in the depth direction of the channel 11 can be precisely conformed to the feeding position of the particulates. Accordingly, it is possible to accurately irradiate the particulates with the measuring light and thereby to obtain a high measurement sensitivity.

Figure 5A:
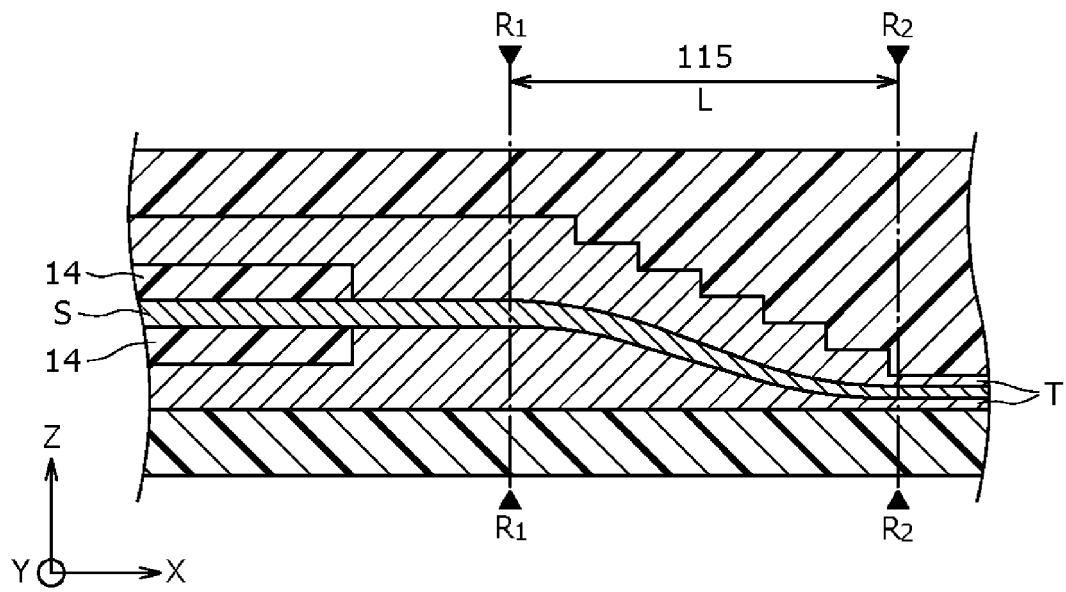
FIGS. 5A and 5B are sectional schematic views showing the configuration of the narrow-down section in which the area in a section orthogonal to the liquid feed direction is reduced stepwise along the liquid feed direction.

Such a narrowing-down of the laminar flow widths of the sheath liquid laminar flow and the sample liquid laminar flow can be achieved also by forming both the channel bottom surface and the channel upper surface of the narrow-down section 115. In addition, as shown in FIG. 5A, in the narrow-down section 115, the channel upper surface (and/or the channel bottom surface) may be formed in a stairway-like shape along the downstream direction. In this case, the narrow-down section 115 is formed in a stairway-like shape of being reduced stepwise in its dimension in the Y-axis direction in top plan view, also. When the narrow-down section 115 is so formed that its area in section orthogonal to the liquid feed direction is reduced stepwise along the downstream direction of the channel to thereby narrow down the laminar flow widths, a merit is obtained as to forming of the narrow-down section 115.

As will be described later, the forming of the narrow-down section 115 and the like arranged in the microchip 1 is carried out by wet etching or dry etching of a glass-made substrate layer, or by nanoimprint technique or injection molding or cutting of a resin-made substrate layer. In this case, the forming of the narrow-down section 115 in the case where the shape of the narrow-down section 115 is an inclined surface is easier to carry out and, particularly, the forming can be more easily achieved by machining or photolithography, than in the case where the shape is a stairway-like shape.

For example, in the case of machining, for forming the narrow-down section 115 as an inclined surface(s), it may be necessary to perform cutting by repeatedly reciprocating a drill in units of several micrometers, which takes much labor. In addition, the drill is worn more easily, and burrs may be generated at the cut portions. On the other hand, where the narrow-down section 115 is formed in a stairway-like shape having only a few steps, cutting is easy to carry out, the drill is worn little, and burrs are unlikely to be generated. Besides, also in the case of photolithography, forming of the narrow-down section 115 in a stairway-like shape having only a few steps, the numbers of times a CAD process and the photolithographic process are repeated can be largely reduced, and production time and cost can be reduced.

Figure 5B:
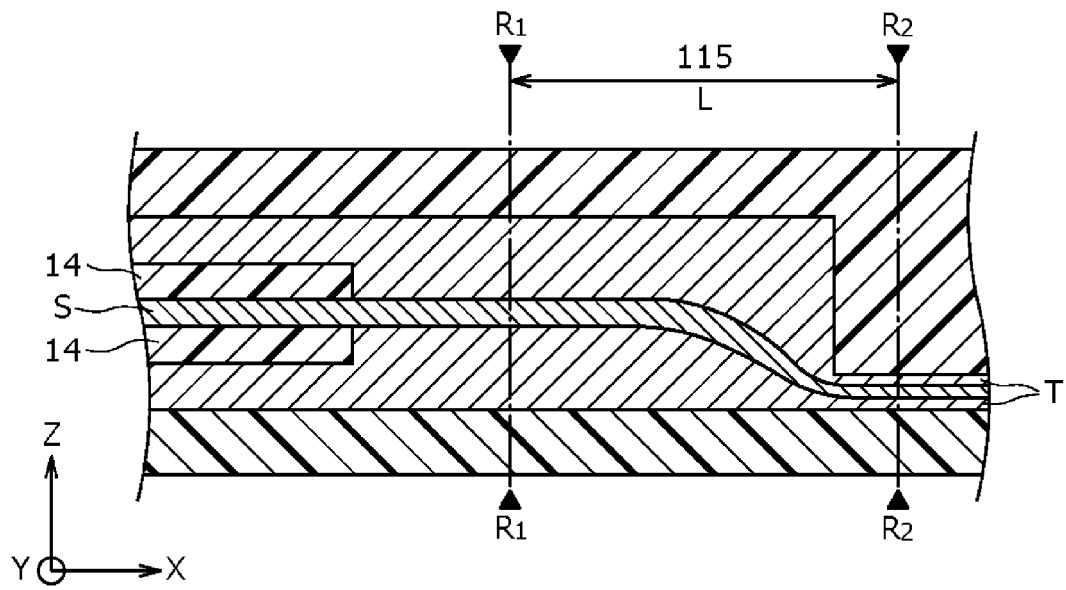

In the case where the narrowing-down is achieved by forming the narrow-down section 115 so that its area in section orthogonal to the liquid feed direction is decreased stepwise along the downstream direction, the area in the orthogonal section can also be reduced to the area corresponding to the laminar flow width after narrowing-down in a single step, as shown in FIG. 5B. It has been confirmed that in this case, also, the sheath liquid laminar flow T and the sample liquid laminar flow S can be narrowed down in the Y-axis and Z-axis directions, without generation of turbulent flow.

Here, it may be contemplated that when the channel 11 is formed as a channel sufficiently small in cross-sectional size and the sample liquid is introduced into the sheath liquid laminar flow passing through the channel 11 by use of a microtube 14 small in diameter, it is possible to form the sheath liquid laminar flow and a sample liquid laminar flow which are preliminarily narrowed down in laminar flow width. In that case, however, the reduction in the diameter of the microtube 14 generates a problem in that the particulates contained in the sample liquid would clog up the microtube 14.

In the microchip 1, with the narrow-down section 115 provided, the narrowing-down of the laminar flow width can be conducted after the sample liquid laminar flow and the sheath liquid laminar flow are formed by use of the microtube 14 whose diameter is sufficiently large in relation to the diameter of the particulates contained in the sample liquid. Therefore, the problem of clogging-up of the microtube 14 as above-mentioned can be dissolved.

Incidentally, the "particulates" in the present embodiment widely include microscopic bioparticles such as cells, microorganisms, liposome, etc. as well as synthetic particles such as latex particles, gel particles, industrial particles, etc.

The microscopic bioparticles include chromosome, liposome, mitocondria, organelle, etc. which constitute various cells. The cells here include animal cells (blood corpuscle cells, etc.) and plant cells. The microorganisms includes bacteria such as colibacillus, etc., viruses such as tobacco mosaic virus, etc., and fungi such as yeast, etc. Further, the microscopic bioparticles may include also microscopic biopolymers such as nucleic acid, proteins, and complexes thereof. The industrial particles may be, for example, organic or inorganic polymer materials, metals or the like. The organic polymer materials include polystyrene, stylene-vinylbenzene, and polymethyl methacrylate. The inorganic polymer materials include glass, silica, and magnetic materials. The metals include gold colloid and aluminum. The shape of these particulates is usually spherical, but may be non-spherical. Besides, the particulates are not particularly limited as to size, mass or the like.

The inside diameter of the microtube 14 may be set as demanded, according to the diameter of the particulates contained in the sample liquid to be analyzed. For example, where blood is used as the sample liquid and the blood corpuscle cells are to be analyzed, a suitable inside diameter of the microtube 14 is about 10 to 500 μm. In addition, the width and the depth of the channel 11 may be set as demanded, according to the outside diameter of the microtube 14 which reflects the diameter of the particulates to be analyzed. For instance, where the inside diameter of the microtube 14 is about 10 to 500 μm, the width and the depth of the channel 11 are each preferably about 100 to 2000 μm. Incidentally, the cross-sectional shape of the microtube is not limited to circle, and may be an arbitrary shape such as ellipse, quadrilateral, and triangle.

The laminar flow widths of the sheath liquid laminar flow and the sample liquid laminar flow before narrowing-down in the narrow-down section 115 can vary depending on the width and depth of the channel 11 and the diameter of the microtube 14 which are set as above-mentioned. In this case, the laminar flow widths can be narrowed down to arbitrary laminar flow widths by regulating, as demanded, the area in section orthogonal to the liquid feed direction of the narrow-down section 115. For example, in FIG. 2, let the channel length of the narrow-down section 115 be L and the inclination angle of the channel bottom surface be $\theta_Z$, then the narrow-down width of the laminar flow widths of the sheath liquid laminar flow T and the sample liquid laminar flow S in the narrow-down section 115 is $L \cdot \tan \theta_Z$. Therefore, an arbitrary narrow-down width can be set by appropriately regulating the channel length L and the inclination angle $\theta_Z$. Further, let the constriction angles of the channel side walls of the narrow-down section 115 in the Y-axis direction in FIG. 1 be respectively $\theta_{Y1}$ and $\theta_{Y2}$, then by setting these constriction angles to be equal to the inclination angle $\theta_Z$ it is possible to isotropically reduce and narrow down the sheath liquid laminar flow T and the sample liquid laminar flow S as shown in FIGS. 4A and 4B.

4. Manufacturing Method for Microchip 1

As the material of the microchip 1, there may be used glass and various resins (PP, PC, COP, PDMS). In the case where the analysis using the microchip 1 is to be carried out optically, a material is selected which is light-transmitting, shows little self-fluorescence, has a small wavelength dispersion and, hence, has little optical error.

In order to maintain the light-transmitting property of the microchip 1, it is desirable to laminate a so-called hard coat layer, which is ordinarily used in optical disks, on the surface of the microchip 1. If the surface of the microchip 1, particularly, the surface of a light detection section (see the "detection section" in FIG. 7 to be described later) is stained with a fingerprint or the like, the quantity of light transmitted therethrough is reduced, possibly leading to a lowering in the accuracy of optical analysis. When a hard coat layer excellent in transparency and stain-proofing properties is laminated on the surface of the microchip 1, the lowering in the accuracy of analysis can be prevented from occurring.

The hard coat layer (or film) can be formed by use of one of the hard coating agents which are used ordinarily, for example, a UV-curing type hard coating agent admixed with a fingerprint stain-proofing agent such as a fluoro or silicone stain-proofing agent. Japanese Patent Laid-open No. 2003-157579 discloses an active energy ray curable composition (P) as a hard-code agent which contains a multifunctional compound (A) having at least two polymerizable functional groups capable of being polymerized under active energy rays, modified colloidal silica (B) whose average particle diameter is 1 to 200 nm, and whose surface has been modified by a mercaptosilane compound in which an organic group having a mercapto group and a hydrolysable group or hydroxyl group are bonded to silicon atom, and a photopolymerization initiator (C).

Forming of the channel 11 and the like arranged in the microchip 1 can be carried out by wet etching or dry etching of a glass-made substrate layer, or by nanoimprint technique or injection molding or cutting of a resin-made substrate layer. Then, the substrate layer formed with the channel 11 and the like is cover sealed with a substrate layer of a material which is the same as or different from that of the former substrate layer, whereby the microchip 1 can be fabricated.

Figure 6A:
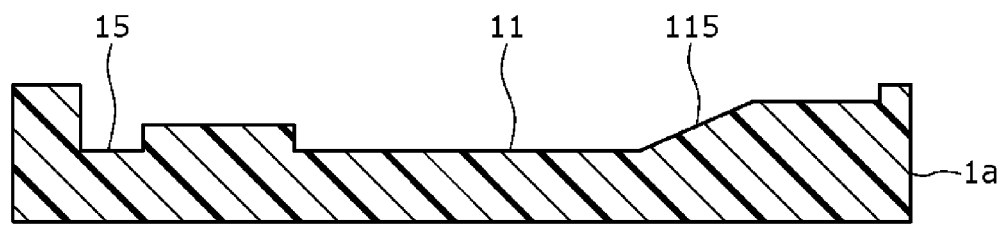
FIGS. 6A to 6C are conceptual diagrams illustrating an example of the method for manufacturing the microchip 1.
Figure 6B:
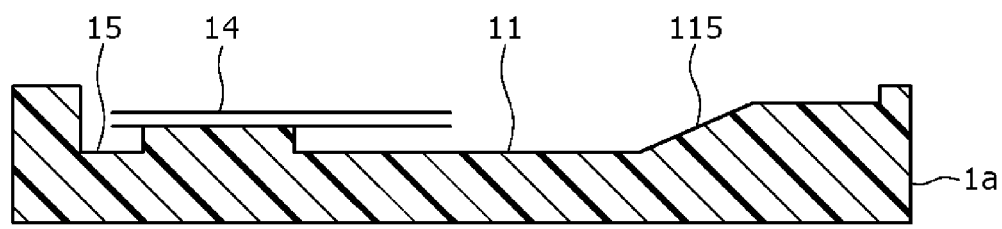
Figure 6C:
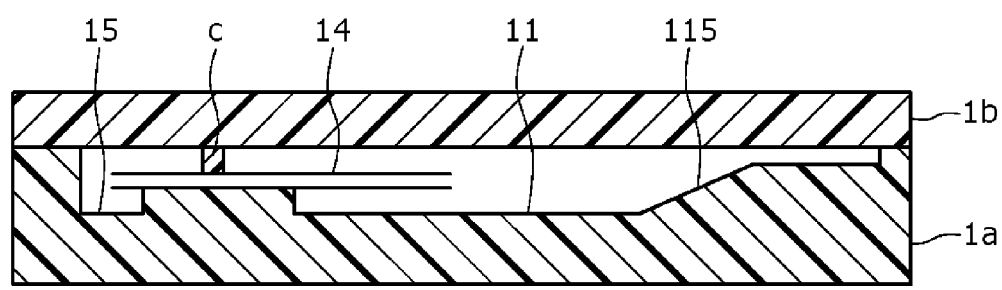

FIGS. 6A to 6C are conceptual diagrams illustrating an example of the method of manufacturing the microchip 1. The microchip 1 can be simply manufactured by forming a single substrate layer by, for example, injection molding in which a mold is used. Incidentally, FIGS. 6A to 6C are sectional schematic views corresponding to section P-P of the magnified view in FIG. 1.

First, a mold provided with the shape of a channel 11 including bent sections 111 to 114 and a narrow-down section 115 and the shapes of a sample liquid inlet 15 and the like is set on an injection molding machine, and transfer of shape to a substrate layer 1a is conducted. The substrate layer 1a thus injection molded is provided with the shape of the channel 11 including the bent sections 111 to 114 and the narrow-down section 115 and the shapes of the sample inlet 15 and the like (see FIG. 6A).

Next, as shown in FIG. 6B, a microtube 14 is disposed. The microtube 14 is disposed in the manner of fitting it into a groove which is formed between the sample inlet 15 and the channel 11 in the manner of connecting them to each other so that a sample liquid introduced into the sample inlet 15 will be fed through the microtube 14 into the channel 11.

After the microtube 14 is thus arranged, the substrate layer 1a and a substrate layer 1b are laminated onto each other, as shown in FIG. 6C. The lamination of the substrate layer 1a and the substrate layer 1b onto each other can be carried out by appropriately using a known method. For example, heat fusing, adhesion with an adhesive, anodic bonding, bonding by use of a pressure sensitive adhesive-coated sheet, plasma-activated bonding, ultrasonic bonding, etc. can be used, as demanded. In FIG. 6C, symbol c denotes an adhesive for fixing the microtube 14 to the substrate layers 1a and 1b. This adhesive 143 functions also to seal the groove in which the microtube 14 is fitted, so as to separate the sample liquid inlet 15 and the channel 11 from each other. As a result, the sample liquid inlet 15 and the channel 14 communicate with each other only through the inside of the microtube 14, whereby the sample liquid introduced into the sample liquid inlet 15 will be fed through the microtube 14 into the channel 11.

The microchip 1 obtained by the above-described method can be used irrespectively of the orientation (face/back) thereof. Therefore, the microchip 1 shown in FIG. 6C can naturally be used also in the condition where the substrate layer 1a is on the upper side and the substrate layer 1b on the lower side. In the condition of FIG. 6C, the narrow-down section 115 is so formed that the channel bottom surface thereof is an inclined surface which gradually becomes higher along the downstream direction. When the microchip 1 is reversed face side back, however, the narrow-down section 115 can be deemed to have its channel upper surface formed as an inclined surface which becomes lower in the channel depth direction along the downstream direction. In this case, the sheath liquid laminar flow and the sample liquid laminar flow fed into the narrow-down section 115 are narrowed down in laminar flow width while being deflected toward the lower side of the microchip 1. This applies also to the case where the channel upper surface (and/or the channel bottom surface) of the narrow-down section 115 is formed in a stairway-like shape, as has been described referring to FIGS. 5A and 5B.

As the microtube 14, tubes made of glass, ceramics or various resins (PP, PC, COP, PDMS) can be adopted, and the material is not particularly limited. As an example, a silica tube can be adopted as the microtube 14. Silica tubes with an inside diameter in the range of several tens of micrometers to several hundreds of micrometers are commercially available, so that a tube with a suitable diameter can be utilized. Since silica tubes have high heat resistance, by use of a silica tube it is possible to form a microchip which is stable at the time of thermocompression bonding of a substrate layer.

Where a metallic tube is adopted as the microtube 14, an electric charge can be given through the microtube 14 to the sample liquid flowing through the inside thereof. Consequently, for example, a microchip 1 can be provided with "a particulate measuring section for measuring the particulates introduced, at least two particulate fractionating channels disposed on the downstream side of the particulate measuring section so as to perform fractional collection of the particulates, and at least two electrodes disposed in the vicinity of channel ports opening from the particulate measuring section into the particulate fractionating channels so as to control the moving direction of the particulates" described in Patent Document 1, thereby performing fractionation of the particulates.

In addition, the microchip according to an embodiment, like a microchip 3 to be described later, can be provided with at least one fluid introduction section which joins the channel 11 from at least one lateral side and through which either fluid of a gas and an insulating liquid is introduced into the channel 11. The fluid introduction section also is formed by wet etching, dry etching, nanoimprint technique, injection molding, or machining, in the same manner as the channel 11 and the like.

5. Method of Fractionating Particulates by Microchip (5-1) Microchip 2

Figure 7:
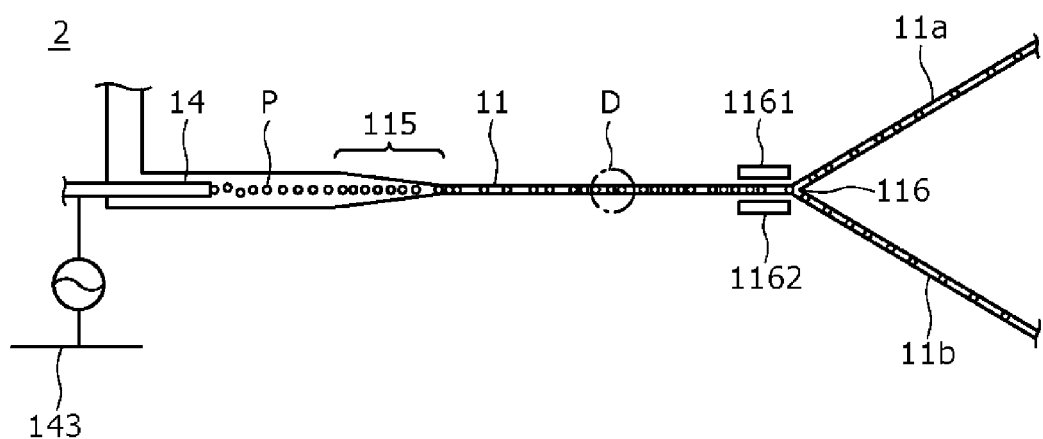
FIG. 7 is a conceptual diagram illustrating a method for fractionating particulates contained in a sample liquid by use of a microchip 2 according to an embodiment wherein a microtube is formed from a metal permitting a voltage to be impressed thereon.

FIG. 7 is a conceptual diagram illustrating a method of fractionating particulates contained in a sample liquid by use of a microchip 2 having a microtube 14 formed from a metal permitting a voltage to be impressed thereon. The microchip 2 has the same configuration as that of the microchip 1, except for the configuration specifically described below.

A channel 11 in the microchip 2 is provided with branch channels 11a, 11b branched at a branching section 116 on the downstream side of a narrow-down section 115, and the particulates contained in the sample liquid introduced via the microtube 14 into the channel 11 can be selectively fed into one of the branch channels 11a, 11b.

In FIG. 7, symbol 143 denotes a charging section for impressing a voltage on the microtube 14. The charging section 143 gives a positive or negative electric charge to the sample liquid containing the particulates which flows through the inside thereof. The control of the feed direction of the particulates at the branching section 116 can be conducted based on the electric charge given to the sample liquid containing the particulates by the charging section 143.

More specifically, for example, a slight pressure difference is applied to the microtube 14 at the time of introducing the sample liquid into the channel 11, whereby the sample liquid is fed into a sheath liquid laminar flow, which is passing through the channel 11, in the form of droplets P each of which contains one particulates or a predetermined number of particulates, as shown in FIG. 7. Simultaneously, the polarity of the voltage impressed on the charging section 143 is switched, whereby a positive or negative electric charge is imparted to each of the droplets P being fed into the sheath liquid laminar flow. In this instance, for electrically insulating the droplets P from each other, an electrically insulating liquid is desirably used as the sheath liquid.

As the method for applying a pressure difference to the microtube 14, there can be adopted, for example, a method in which a piezoelectric element (micro-vibration element) capable of micro-vibration is arranged in contact with the microtube 14, and a method in which a piezoelectric element is disposed to front on the inside of a sample liquid inlet 15.

Figure 8:
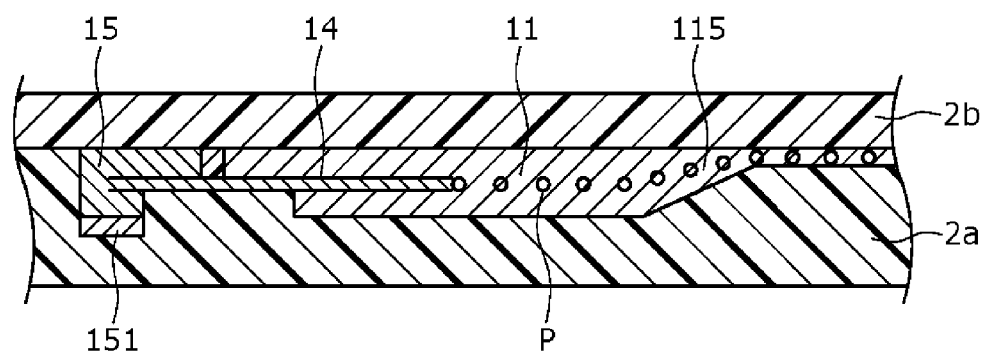
FIG. 8 is a sectional schematic view illustrating a layout position of a piezoelectric element for dropletizing the sample liquid in the microchip 2.

FIG. 8 illustrates a layout position of a piezoelectric element for dropletizing the sample liquid. The figure is a sectional schematic view corresponding to FIG. 6C. Here, a case where the piezoelectric element is arranged at the bottom surface of the sample liquid inlet 15 is shown.

In the figure, the piezoelectric element denoted by symbol 151 is arranged at the bottom surface of the sample liquid inlet 15 in the state of fronting on the inside of the sample liquid inlet 15. When a voltage is impressed thereon, the piezoelectric element 151 deforms so as to exert a pressure on the sample liquid flowing through the sample liquid inlet 15. By this pressure, a pressure is also exerted on the sample liquid in the microtube 14 communicating with the sample liquid inlet 15. In this case, a pulsed voltage is used as the voltage impressed on the piezoelectric element 151 so as to vibrate the piezoelectric element 151, whereby the pressure exerted on the sample liquid in the microtube 14 is varied periodically. As a result, the sample liquid is discharged from the microtube 14 into the channel 11 in the form of droplets (in a dropletized state).

Such a dropletizing by use of a piezoelectric element 151 can be performed, for example, in the same manner as ink droplet ejection by use of piezo-vibration elements which is adopted in ink jet printers. While the case where the piezoelectric element 151 is disposed to front on the inside of the sample liquid inlet 15 has been described here, other configurations may also be adopted. For example, a configuration may be adopted in which the piezoelectric element 151 is disposed in contact with an outer wall of the microtube 14, and a pressure arising from deformation of the piezoelectric element 151 is exerted directly on the microtube 14, thereby dropletizing the sample liquid. Incidentally, a signal impressed on the piezoelectric element for applying the pressure difference and a signal impressed for applying a voltage on the microtube 14 are synchronized, whereby formation of a droplet and electric charging (electrification) of the droplet can be performed at an arbitrary timing.

At the branching section 116, a pair of electrodes 1161 and 1162 are oppositely arranged on both sides of the channel 11 (see FIG. 7). The electrodes 1161, 1162 are capable of electric charging in positive or negative polarity, and they guide the droplet P into either of the branch channels 11a and 11b by an electrical repelling force (or attracting force) generated between the electric charge given to the droplet P and the electric charges thereof. The electrodes 1161, 1162 may be preliminarily arranged in the microchip 2, or, alternatively, they may be arranged in a particulate fractionating apparatus on which the microchip 2 is to be mounted, in such a manner that they are located at the branching section 116 of the microchip 2 thus mounted. Further, the electrodes 1161, 1162 may be provided by a configuration in which those portions of the branch channels 11a, 11b in the vicinity of the branching section 116 are composed of metallic tubes and the metallic tubes function as electrodes, as in the microchip 3 to be described later.

Figure 9A:
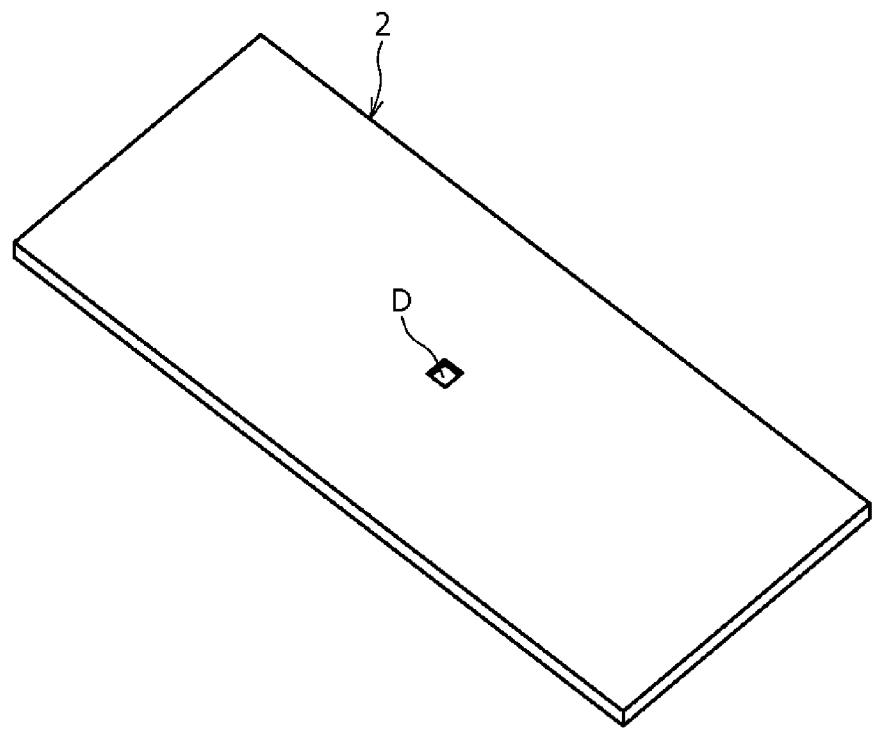
FIGS. 9A and 9B are simplified perspective view showing configurations of the microchip 2 in which a surface of a detection section is partly recessed.
Figure 9B:
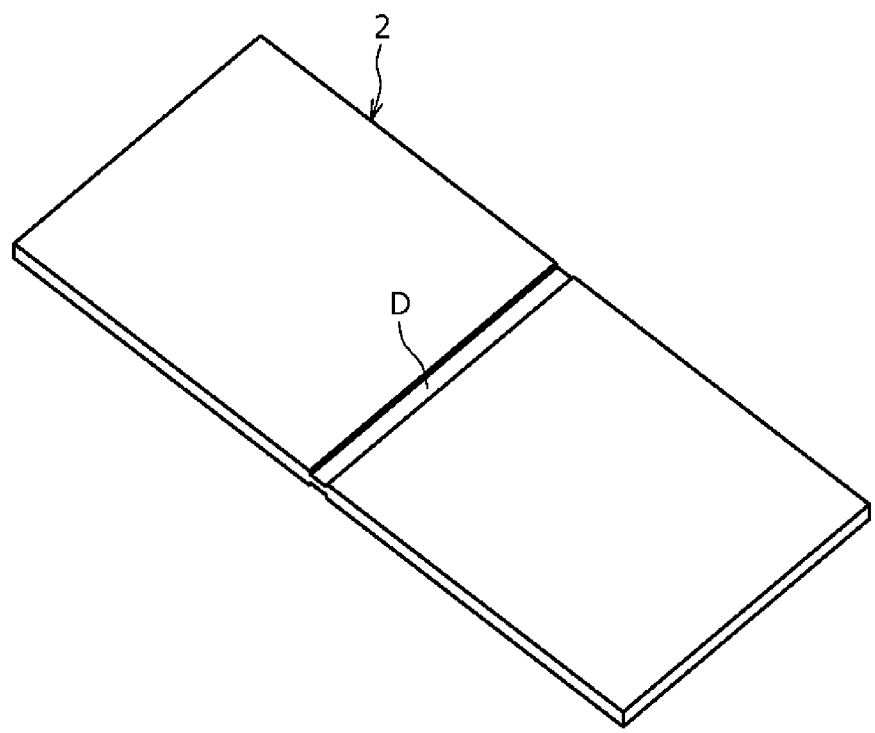

The fractionation of particulates is conducted based on the results of determination of the characteristics of the particulates, at a detection section denoted by symbol D in FIG. 7. Here, description will be made of an exemplary case in which the detection section D is configured as an optical detection system, and light generated upon irradiation of the particulates in an introduction channel 11 with a laser beam is detected, thereby determining the characteristics of the particulates. The optical detection system and the particulate fractionating apparatus may be configured in the same manner as those in particulate analysis systems using microchips according to the related art. Specifically, the optical detection system includes: a laser beam source; a condenser lens, a dichroic mirror, a bandpass filter and the like for condensing the laser beam to irradiate a particulate therewith; and a detector for detecting the light generated upon irradiation of the particulate with the laser beam. As the detector, for example, a PMT (photo multiplier tube), CCD (charge-coupled device) or CMOS (complementary metal-oxide semiconductor) device or the like area image pick-up element may be used.

Where the detection section D is configured as an optical detection system, a countermeasure against the lowering in accuracy of analysis due to staining with a fingerprint or the like as above-mentioned is desirably provided. For example, as shown in FIGS. 9A and 9B, the surface of the detection section D may be recessed as compared with the surface of the other portions of the microchip 2, thereby preventing a fingertip or dirt from coming into contact with the surface of the detection section. FIG. 9A shows the case where the surface of the microchip 2 is formed with a dent (recess) in the area of the detection section D, while FIG. 9B shows the case where the surface of the microchip 2 is formed with a groove including the surface in the area of the detection section D.

A parameter for determination of optical characteristics of the particulates may be selected according to the particulates under consideration and the purpose of fractionation, from among forward scattered light for measurement of size of particulates, side-way scattered light for measurement of structure, and scattered light, fluorescent light and the like arising from Reyleigh scattering, Mie scattering or the like. The detection section D analyzes the light detected according to such a parameter, and determines whether or not the particulate in question has a predetermined optical characteristic.

Then, for example in the case where the electric charge given by the charging section 143 to the droplet P of the sample liquid containing the particulate is positive in polarity, when the particulate is determined to have a predetermined optical characteristic, the electrode 1161 is electrically charged in negative polarity and the electrode 1162 in positive polarity so that the droplet P is guided into the branch channel 11a by the electrical repelling force. On the contrary, when the particulate is determined not to have the predetermined optical characteristic, the electrode 1161 is electrically charged in positive polarity and the electrode 1162 in negative polarity so that the droplet is guided into the branch channel 11b by the electrical repelling force. By this process, only the particulates having the predetermined optical characteristic can be guided into the branch channel 11a, to be fractionally collected.

Thus, in the microchip 2, with the microtube 14 formed from a metal, the sample liquid droplet P containing the particulate can be fed into the center of the sheath liquid laminar flow T passing through the channel 11 and can simultaneously be given an electric charge, and, based on the electric charge, fractionation of the particulates can be achieved.

Besides, in the microchip 2, the sheath liquid laminar flow and the sample liquid droplets P can be fed to the detection section D while narrowing down the laminar flow widths of them in the horizontal and vertical directions of the microchip 2, whereby the focal position of the measuring light can be precisely conformed to the feeding position of the particulate. Therefore, the particulates can be accurately irradiated with the measuring light, and optical characteristics of the particulates can be detected with high sensitivity.

Furthermore, in the microchip 2, the particulate-containing sample liquid droplets P can be arrayed substantially in one row in the narrowed-down laminar flow, by the microtube 14 and the narrow-down section 115. With the droplets P arrayed substantially in one row, it is easy for the electrical repelling force from the electrodes 1161, 1162 at the branching section 116 to be applied to the droplet P which contains the particulate having the predetermined characteristic. Besides, with the laminar flow widths at the branching section 116 having been sufficiently narrowed down, the droplets P can be guided into the branch channel 11a or 11b by only exerting thereon a weak repelling force by the electrodes 1161, 1162.

While the case where the detection section D is configured as an optical detection system and the characteristics of particulates are measured optically has been described here, the measurement of characteristics of particulates can also be performed electrically or magnetically. Specifically, in the case where electric properties and magnetic characteristics of particulates are measured, micro-electrodes may be arranged at the detection section D to thereby measure, for example, resistance, capacitance, inductance, impedance, variation in electric field between the electrodes, or the like, or, alternatively, magnetization, variation in magnetic field, or the like as to the particulates may be measured. Also, two or more of these characteristics may be measured at the same time. For example, in the case where magnetic beads or the like labeled by a fluorescent coloring matter are to be measured as the particulates, measurement of optical characteristic(s) and measurement of magnetic characteristic(s) are performed simultaneously.

According to the microchip 2, it is possible, even in the case of measuring electric or magnetic characteristic of particulates, to precisely conform the measuring position of micro-electrodes arranged at the detection section D to the feeding position of the particulates, and to detect the characteristics of the particulates with high sensitivity.

(5-2) Microchip 3

Now, description will be made below of a method of fractionating particulates contained in a sample liquid, by use of a microchip 3 provided with at least one fluid introduction section which joins a channel 11 from at least one lateral side so as to introduce either fluid of a gas and an insulating liquid into the channel 11.

Figure 10:
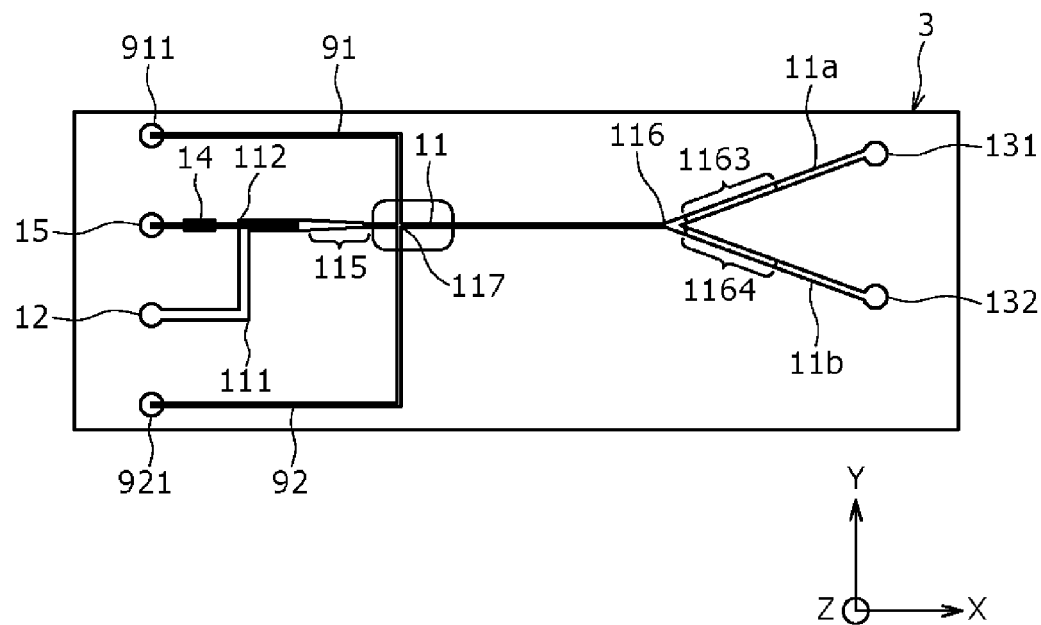
FIG. 10 is a simplified top plan view showing the configuration of a microchip 3 according to an embodiment.

FIG. 10 is a simplified top plan view showing the configuration of the microchip 3 according to an embodiment. The microchip 3 is the same as the microchip 1 and the microchip 2 in configuration, except for the configuration specifically described below.

In FIG. 10, symbols 91 and 92 denote fluid introduction sections for introducing either fluid of a gas and an insulating liquid into the channel 11. The fluid introduction sections 91, 92 communicate with the channel 11 at one-side ends thereof, and are provided at other-side ends thereof with fluid inlets 911, 912 which are each supplied with a fluid. A gas or insulating liquid (hereinafter referred to as "a gas or the like") supplied into the fluid introduction sections 91, 92 through the fluid inlets 911, 912 by a booster pump (not shown) is introduced into the channel 11 at a joining section denoted by symbol 117.

In the microchip 3, a liquid flowing through the channel 11 can be split into droplets (be dropletized) by the fluid introduced into the joining section 117 via the fluid introduction sections 91, 92, and the droplets can be fed to a branching section 116 of branch channels 11a, 11b.

Figure 11A:
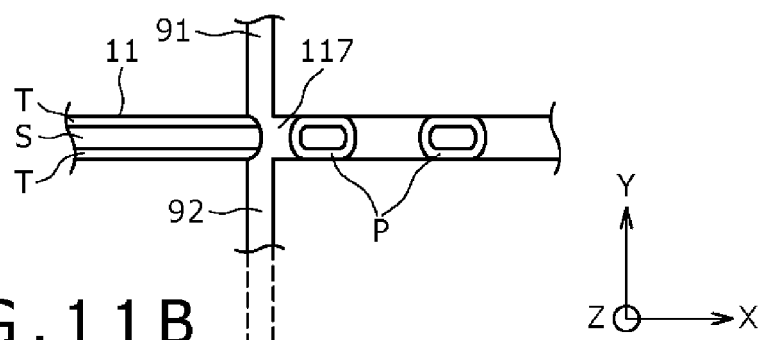
Figure 11B:
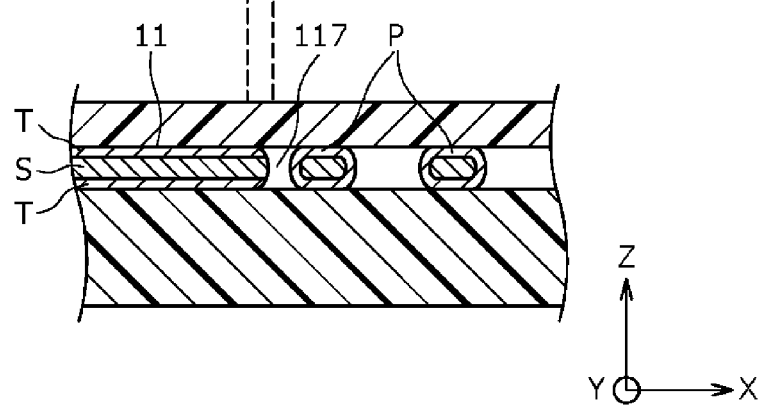

FIGS. 11A and 11B are schematic views showing the joining section 117 in a magnified form. FIG. 11A is a top plan view, and FIG. 11B is a ZX sectional view including a microtube 14. The figures show the case where a sheath liquid laminar flow T and a sample liquid laminar flow S fed through the microtube 14 and a narrow-down section 115 to the joining section 17 are split into droplets.

Specifically, at the joining section 117, a gas or the like is introduced into the sheath liquid laminar flow T and the sample liquid laminar flow S being fed, from the fluid introduction sections 91, 92 at a predetermined timing. As a result, the sheath liquid laminar flow T and the sample liquid laminar flow S are split into droplets, as shown in the figures, by the gas or the like introduced thereinto. By this process, the sheath liquid laminar flow T and the sample liquid laminar flow S can be fed to the branching section 116 after being split into the droplets in the channel 11 (see the droplets P in FIGS. 11A and 11B). Where a particulate-containing liquid is let flow as the sample liquid and a gas or the like is introduced into the liquid at a predetermined timing, it is possible to form droplets P each of which contains one particulate or a predetermined number of particulates.

While the case where one fluid introduction section is provided on each lateral side of the channel 11 has been shown in FIGS. 10, 11A and 11B, it suffices that the fluid introduction section is provided on at least one lateral side of the channel 11. Further, at the joining section 117, more than two fluid introduction sections may be arranged to join the channel 11. In addition, while the fluid introduction sections joint the channel 11 at right angles in FIGS. 10 and 11, the joining angle of the fluid introduction section(s) can be arbitrarily set.

In the microchip 2 described above, at the branching section 116, the pair of electrodes 1161 and 1162 have been oppositely arranged on both lateral sides of the channel 11. On the other hand, in the microchip 3 here, a configuration is adopted wherein those portions of the branch channels 11a and 11b in the vicinity of the branching section 116 are composed of metallic tubes 1163 and 1164, and they function as electrodes. The metallic tubes 1163, 1164 can be electrically charged in positive or negative polarity, and they guide each droplet P into either of the branch channels 11a, 11b by an electrical repelling force (or attracting force) acting between the electric charge given to the droplet P and the electric charges thereof.

Specifically, as has been described referring to the microchip 2, in the case where the electric charge given by a charging section 143 (see FIG. 7) to the sample liquid droplet P containing the particulate is positive in polarity, when the particulate under consideration is determined to have a predetermined optical characteristic, the metallic tube 1163 is electrically charged in negative polarity and the metallic tube 1164 in positive polarity so that the droplet P is guided into the branch channel 11a by the electrical repelling force. On the other hand, when the particulate in question is determined not to have the predetermined optical characteristic, the metallic tube 1163 is electrically charged in positive polarity and the metallic tube 1164 in negative polarity so that the droplet is guided into the branch channel 11b by the electrical repelling force. Incidentally, in the figure, symbols 131 and 132 denote outlets through which the particulates fractionally collected respectively into the branch channels 11*a*, 11*b* are taken out to the exterior of the microchip 3.

Thus, in the microchip 3, with the fluid introduction sections 91 and 92 provided, the particulate-containing sample liquid can be split into droplets and, simultaneously, given an electric charge by the microtube 14, and, based on the electric charge, fractionation of the particulates can be achieved.

In order to maintain the electric charges given to the sample liquid droplets formed in the channel 11, a gas is preferably used as the fluid introduced via the fluid introduction sections 91, 92. In this case, if the splitting of the sheath liquid laminar flow and the sample liquid laminar flow in the channel 11 is unsatisfactory and the adjacent droplets become partly continuous with each other, the electric charges given to the droplets would disappear. In such a case, it may be impossible to control the liquid feed direction in the branching section 116 or the control may be inaccurate. Therefore, in order to satisfactorily split the sheath liquid laminar flow and the sample liquid laminar flow by the introduced gas and to maintain the electrical insulation between the split droplets, it is desirable to impart water repellency to the surface of the channel 11 (particularly, to the channel portion on the downstream side of the joining section 117). Further, it is effective to impart electrical insulating properties to the surface of the channel 11 so as to inhibit transfer of electric charges between the split droplets. The electrical insulating properties can be imparted, for example, by coating the channel surface with an insulating material or forming a film of an insulating material on the channel surface. In addition, inhibition of electric current flow between the droplets can also be achieved by letting an insulating liquid such as ultrapure water along the channel surface.

Besides, in order to maintain the electric charges of the sample liquid droplets formed in the channel 11, an electrically insulating liquid ("insulating liquid") may be used as the fluid. As the insulating liquid, for example, the above-mentioned ultrapure water or the like may be used. This makes it possible to inhibit transfer of electric charges between the split droplets.

6. Fluid Analyzing Apparatus (Particulate Fractionating Apparatus)

Figure 12:
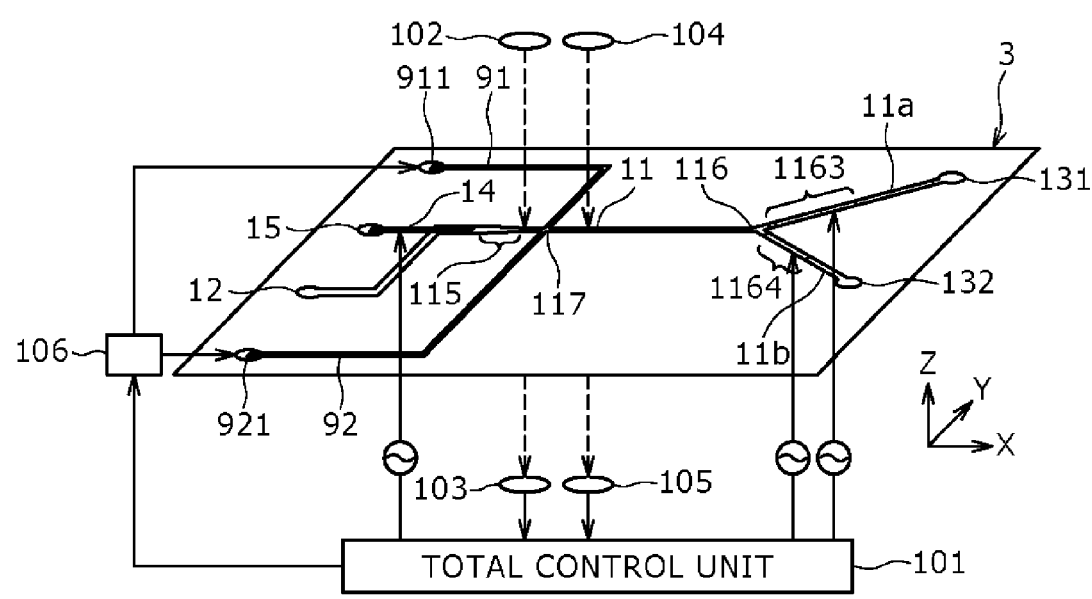
FIG. 12 is a schematic view illustrating the configuration of a fluid analyzing apparatus (particulate fractionating apparatus) according to an embodiment.
Figure 13A:
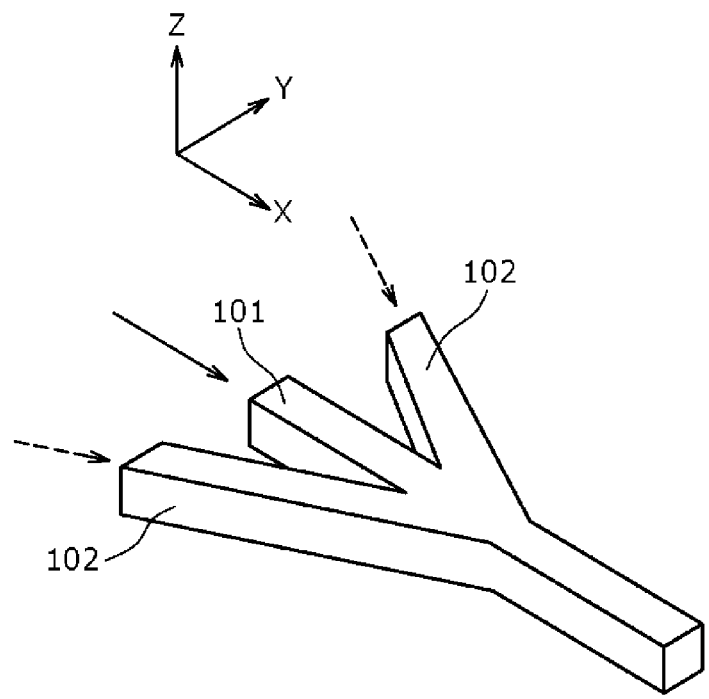
FIGS. 13A and 13B are simplified perspective views showing an ordinary trifurcated channel structure (FIG. 13A) and the state of a fluid laminar flow formed thereby (FIG. 13B).
Figure 13B:
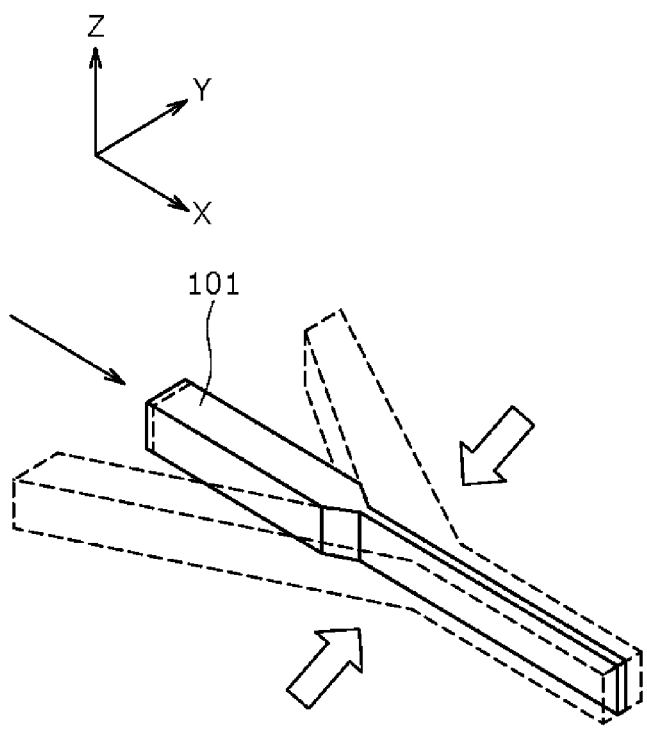

FIG. 12 is a schematic diagram illustrating the configuration of a fluid analyzing apparatus according to an embodiment. The fluid analyzing apparatus is preferable for use as a particulate fractional collection apparatus which analyzes characteristics of particulates and fractionates the particulates on the basis of the analytical results. Each of configurations of the fluid analyzing apparatus (particulate fractional collection apparatus) will be described below with reference to an exemplary case where the above-described microchip 3 is mounted on the apparatus.

The particulate analyzing apparatus shown in FIG. 12 includes: an optical detection system (an irradiation section 102, a detection section 103) for detecting the particulates passing through the channel 11 on the upstream side of the joining section 117 in the microchip 3; an optical detection system (an irradiation section 104, a detection section 105) for determining optical characteristics of the particulates on the downstream side of the joining section 117; and a booster pump 106 for supplying a gas or the like into fluid inlets 911, 921 of the microchip 3. In the figure, symbol 101 denotes a total control unit for controlling these optical detection systems and the booster pump as well as the voltages impressed respectively on the microtube 14 and on the metallic tubes 1163, 1164.

Further, the particulate fractional collection apparatus has liquid supply means (not shown), whereby a sheath liquid laminar flow is supplied via the sheath liquid inlet 12 of the microchip 3, and a sample liquid laminar flow is supplied via the sample liquid inlet 15. The sheath liquid and the sample liquid supplied into the microchip 3 are fed to the joining section 117 after being so conditioned that the sample liquid laminar layer is surrounded by the sheath liquid laminar layer and that the laminar flow widths are narrowed down under the functions of the microtube 14 and the narrow-down section 115.

(6-1) Detection of Particulates

The particular fractional collection apparatus has an optical detection system for optical detection of the particulates contained in the sample liquid laminar flow, on the upstream side of the joining section 117. This optical detection system can be configured in the same manner as those in particulate analyzing systems using microchips according to the related art. Specifically, the optical detection system includes a laser beam source, an irradiation section 102 composed of a condenser lens and the like for condensing the laser beam and irradiating each of the particulates with the laser beam, and a detection system 103 for detecting the light generated from the particulate upon irradiation with the laser beam by use of a dichroic mirror, a bandpass filter and the like. The detection section includes, for example, a PMT (photo multiplier tube), CCD or CMOS device or the like area image pick-up element.

In the microchip 3, the laminar flow widths of the sheath liquid laminar flow and the sample liquid laminar flow can be narrowed down by the narrow-down section 115, before feeding the laminar flows to a laser light irradiation location of the irradiation section 102. Therefore, the focal position of the laser beam radiated from the irradiation section 102 and the feed position of the particulate in the channel 11 can be precisely conformed to each other. This makes it possible to accurately irradiate each particulate with the laser beam, and thereby to detect the particulates with high sensitivity.

The light generated from the particulate and detected by the detection section 103 is converted into an electrical signal, which is outputted to the total control unit 101. The light to be detected by the detection section 103 may be forward scattered light or side-way scattered light from the particulates, or scattered light, fluorescent light or the like arising from Reyleigh scattering, Mie scattering or the like.

The total control unit 101 detects the particulate in the sample liquid laminar flow fed through the channel 11, based on the electrical signal. Then, the total control unit 101 controls the booster pump 106 at a predetermined timing so as to introduce a gas or the like into the joining section 117 through the fluid inlets 911, 921 and the fluid introduction sections 91, 92, thereby splitting the sheath liquid laminar flow and the sample liquid laminar flow into droplets (see FIGS. 11A and 11B).

As for the timing of introduction of the fluid into the joining section 117, the gas or the like is introduced at regular time intervals, for example, each time one particulate is detected, based on the electrical signal from the detection section 103. The period of time from the detection of the particulate to the introduction of the fluid is determined by the distance between the laser beam irradiation location of the irradiation section 102 and the joining section 117 and the feed rate of the sample liquid in the channel 11. By appropriately regulating this period of time and introducing the gas or the like into the joining section 117 each time one particulate is detected, the sheath liquid laminar flow and the sample liquid laminar flow can be split into droplets on a one-particulate basis.

In this case, each of the droplets contains one particulate. The number of the particulate(s) contained in each droplet, however, can be arbitrarily set by regulating, as demanded, the timing of introducing the fluid into the joining section 117. Specifically, by introducing the gas or the like each time a predetermined number of particulates have just been detected, the predetermined number of particulates can be contained into each of the droplets.

Here, description has been made of the case where detection of the particulates contained in the sample liquid laminar flow is performed by an optical detection system. The means of detecting the particulates is not limited to the optical means, and electrical or magnetic means can also be used. In the case of electrically or magnetically detecting the particulates, micro-electrodes may be arranged on the upstream side of the joining section 117 to thereby measure, for example, resistance, capacitance, inductance, impedance, variation in electric field between the electrodes, or the like, or, alternatively, magnetization, variation in magnetic field, or the like as to the particulates may be measured. Then, the measurement result is outputted as an electrical signal, and, based on the signal, detection of the particulates is performed by the total control unit 101.

In the microchip 3, even in the case of electrically or magnetically detecting the particulates, it is possible to precisely conform the measuring position of the micro-electrodes thus arranged and the feed position of the particulate to each other, and thereby to detect the particulates with high sensitivity.

Incidentally, in the case where the particulates have magnetism, a configuration may be considered in which, particularly, the metallic tubes 1163 and 1164 are composed as magnetic poles, whereby the feed direction of the particulates at the branching section 116 is controlled based on a magnetic force.

(6-2) Determination of Optical Characteristics of Particulates

The particulate fractional collection apparatus has an optical detection system including an irradiation section 104 and a detection section 105, also on the downstream side of the joining section 117. This optical detection system is for determination (discrimination) of the characteristics of the particulates. The irradiation section 104 and the detection section 105 may be the same in configuration as the irradiation section 102 and the detection section 103 described above.

The irradiation section 104 radiates a laser beam to each of the particulates contained in the droplets formed at the joining section 117. The light generated from the particulate upon the irradiation is detected by the detection section 105. The light detected by the detection section may be forward scattered light or side-way scattered light from the particulate, or scattered light, fluorescent light or the like arising from Reyleigh scattering, Mie scattering or the like, such light being converted into an electrical signal, which is outputted to the total control unit 101.

Based on the electrical signal inputted, the total control unit 101 determines (discriminates) the optical characteristics of the particulates while taking as a parameter the forward scattered light or side-way scattered light from the particulates or the scattered light or fluorescent light arising from Reyleigh scattering, Mie scattering or the like. The parameter for determination of the optical characteristics is selected according to the particulates under consideration and the purpose of fractional collection. Specifically, forward scattered light is adopted in the case of determining the size of the particulates, side-way scattered light is adopted in the case of determination of structure, and fluorescent light is adopted in the case of determining whether a fluorescent material labeling the particulate is present or absent.

The total control unit 101 analyzes the light detected according to the parameter(s), to determine whether the particulate in question has the predetermined optical characteristic(s).

Here, description has been made of the case where the characteristics of the particulates contained in the droplets are optically determined. However, the determination of the characteristics of particulates can also be performed electrically or magnetically. In the case of measuring the electrical properties and magnetic characteristics of the particulates, micro-electrodes may be arranged on the downstream side of the joining section 117 to thereby measure, for example, resistance, capacitance, inductance, impedance, variation in electric field between the electrodes, or the like, or, alternatively, magnetization, variation in magnetic field, or the like as to the particulates may be measured. Two or more of these characteristics may be measured at the same time. For example, in the case where magnetic beads or the like labeled by a fluorescent coloring matter are to be measured as the particulates, measurement of optical characteristic(s) and measurement of magnetic characteristic(s) are performed simultaneously.

(6-3) Fractional Collection of Particulates

Based on the determination results of the characteristics of the particulates, the total control unit 101 controls the voltages to be impressed respectively on the microtube 14 and on the metallic tubes 1163, 1164 based on the determination result of the characteristics of the particulates so that the droplets containing the particulates having the predetermined characteristic(s) are guided into either of the branch channels 11a and 11b, whereby fractionation or fractional collection of the particulates is performed.

For example, in the case where the particulate contained in the droplet is determined to have a predetermined characteristic, when the droplet containing the particulate under consideration is given a positive electric charge by the microtube 14, the metallic tube 1163 is electrically charged in negative polarity and the metallic tube 1164 in positive charge. By this, the moving direction of the droplet at the branching section 116 is guided into the branch channel 11a. In this manner, the particulates having the predetermined characteristic are collected through the outlet 131.

On the contrary, when the particulate contained in the droplet under consideration is determined not to have the predetermined characteristic, the metallic tube 1163 is electrically charged in positive polarity and the metallic tube 1164 in negative polarity, whereby the droplet is guided into the branch channel 11b, and the particulate is discharged via the outlet 132.

Thus, in the particulate fractionating apparatus according to an embodiment, according to the detection result of the characteristic(s) of each particulate, the electric charge to be given to the droplet containing the particulate and the voltage to be impressed between the electrodes are appropriately switched to positive or negative polarity under control, whereby the particulate under consideration can be guided into one branch channel selected arbitrarily, and fractional collection is achieved.

Here, the optical detection system (the irradiation section 102, the detection section 103) for detecting the particulate in the sample liquid laminar flow passing through the channel 11 and for performing dropletization and the optical detection system (the irradiation section 104, the detection section 105) for determining the optical characteristic of the particulate contained in the droplet have been separately provided respectively on the upstream side and the downstream side of the joining section 117, but these optical detection systems may be configured integrally.

It should be understood that various changes and modifications to the presently preferred embodiments described herein will be apparent to those skilled in the art. Such changes and modifications can be made without departing from the spirit and scope of the present application and without diminishing its intended advantages. It is therefore intended that such changes and modifications be covered by the appended claims.

The invention is claimed as follows:

1. A microchip comprising:
two substrates each having a main surface extending in a y-axis direction and an x-axis direction;
a channel formed between the substrates;
a sample inlet provided on at least one of the substrates, the sample inlet configured to permit a sample liquid to be introduced into the channel; and
a sheath inlet provided on at least one of the substrates, the sheath inlet configured to permit a sheath liquid to be introduced into the channel,
wherein the channel is configured to permit the sheath liquid and the sample liquid to flow therethrough in a positive x-axis direction such that a laminar flow of the sample liquid is surrounded by a laminar flow of the sheath liquid therein, the channel having first walls opposed to one another in a z-axis direction perpendicular to the main surfaces of the substrates, and the channel having second walls opposed to one another in the y-axis direction,
wherein the channel includes a narrow-down section, the first walls and the second walls have inclined surfaces extending in the x-axis direction therein so that a cross sectional area of the channel perpendicular to the x-axis direction is reduced in the positive x-axis direction, and
wherein the inclined surface of one of the first walls extends in a positive z-axis direction in the positive x-axis direction, and the inclined surface of the other of the first walls extends in a negative z-axis direction in the positive x-axis direction.

2. The microchip according to claim 1, wherein the inclined surface of one of the second walls extends in a positive y-axis direction in the positive x-axis direction, and the inclined surface of the other of the second walls extends in a negative y-axis direction in the positive x-axis direction.

3. The microchip according to claim 1, wherein the inclined surfaces of the first walls and the second walls have the same inclination angles.

4. The microchip according to claim 1, further comprising:
a detection section positioned on a downstream side of the narrow-down section.

5. The microchip according to claim 1, further comprising:
a detection section positioned on a downstream side of the narrow-down section,
wherein a width in the y-axis direction and a height in the z-axis direction of the channel are substantially constant at the detection section.

6. The microchip according to claim 1, further comprising:
an outlet provided on at least one of the substrates that is configured to permit discharging of the sheath liquid and the sample liquid outside the substrates.

7. The microchip according to claim 6, wherein
the channel further includes a bend section positioned on a downstream side of the narrow-down section, and the bend section connects with the outlet.

8. An analyzing apparatus comprising;
a microchip comprising
two substrates each having a main surface extending in a y-axis direction and an x-axis direction,
a channel formed between the substrates,
a sample inlet provided on at least one of the substrates, the sheath inlet configured to permit a sample liquid to be introduced into the channel, and
a sheath inlet provided on at least one of the substrates, the sheath inlet configured to permit a sheath liquid to be introduced into the channel;
a light source configured to irradiate a particulate in a detection section positioned on a downstream side of a narrow-down section;
a light detector configured to detect light generated from the particulate; and a controller configured to determine a characteristics of the particulate based on the detected light,
wherein the channel is configured to permit the sheath liquid and the sample liquid to flow therethrough in a positive x-axis direction such that a laminar flow of the sample liquid is surrounded by a laminar flow of the sheath liquid therein, the channel having first walls opposed to one another in a z-axis direction perpendicular to the main surfaces of the substrates, and the channel having second walls opposed to one another in the y-axis direction,
wherein the channel includes the narrow-down section, the first walls and the second walls have inclined surfaces extending in the x-axis direction therein so that a cross sectional area of the channel perpendicular to the x-axis direction is reduced in the positive x-axis direction, and
wherein the inclined surface of one of the first walls extends in a positive z-axis direction in the positive x-axis direction, and the inclined surface of the other of the first walls extends in a negative z-axis direction in the positive x-axis direction.

9. The analyzing apparatus according to claim 8, wherein
the controller is configured to control a voltage applied to the particle based on at least one characteristic of the particulate.

10. The analyzing apparatus according to claim 8, wherein the inclined surface of one of the second walls extends in a positive y-axis direction in the positive x-axis direction, and the inclined surface of the other of the second walls extends in a negative y-axis direction in the positive x-axis direction.

11. The analyzing apparatus according to claim 8, wherein the inclined surfaces of the first walls and the second walls have the same inclination angles.

12. The analyzing apparatus according to claim 8, further comprising:
a detection section positioned on a downstream side of the narrow-down section.

13. The analyzing apparatus according to claim 8, further comprising:
a detection section positioned on a downstream side of the narrow-down section, wherein a width in the y-axis direction and a height in the z-axis direction of the channel are substantially constant at the detection section.

14. The analyzing apparatus according to claim 8, further comprising:
an outlet provided on at least one of the substrates that is configured to permit discharging of the sheath liquid and the sample liquid outside the substrates.

15. The analyzing apparatus according to claim 14, wherein
the channel further includes a bend section positioned on a downstream side of the narrow-down section, and the bend section connects with the outlet.

16. A liquid feeding method comprising:
introducing a sample liquid into a laminar flow of a sheath liquid flowing through a channel so as to perform liquid feeding, the channel being configured to permit the sheath liquid and the sample liquid to flow therethrough in an x-axis direction such that a laminar flow of the sample liquid is surrounded by a laminar flow of the sheath liquid therein, the channel having first walls opposed to one another in a z-axis direction perpendicular to main surfaces of substrates that house the channel and that extend in an x-axis and a y-axis direction, and the channel having second walls opposed to one another in the y-axis direction,
wherein the channel is configured to permit the sheath liquid and the sample liquid to flow therethrough in a positive x-axis direction such that a laminar flow of the sample liquid is surrounded by a laminar flow of the sheath liquid therein, the channel having first walls opposed to one another in a z-axis direction perpendicular to the main surfaces of the substrates, and the channel having second walls opposed to one another in the y-axis direction,
wherein the channel includes a narrow-down section, the first walls and the second walls have inclined surfaces extending in the x-axis direction therein so that a cross sectional area of the channel perpendicular to the x-axis direction is reduced in the positive x-axis direction, and
wherein the inclined surface of one of the first walls extends in a positive z-axis direction in the positive x-axis direction, and the inclined surface of the other of the first walls extends in a negative z-axis direction in the positive x-axis direction.

\* \* \* \* \*